United States Patent
Bell et al.

(10) Patent No.: US 9,976,158 B2
(45) Date of Patent: May 22, 2018

(54) METHOD AND APPARATUS FOR SYNGAS FERMENTATION WITH HIGH CO MASS TRANSFER COEFFICIENT

(76) Inventors: Peter Simpson Bell, Fayetteville, AR (US); Ching-Whan Ko, Fayetteville, AR (US)

(*) Notice: Subject to any disclaimer, the term of this patent is extended or adjusted under 35 U.S.C. 154(b) by 0 days. days.

(21) Appl. No.: 13/471,827

(22) Filed: May 15, 2012

(65) Prior Publication Data

US 2013/0005014 A1 Jan. 3, 2013

Related U.S. Application Data

(60) Provisional application No. 61/571,564, filed on Jun. 30, 2011, provisional application No. 61/571,565, (Continued)

(51) Int. Cl.
*C12P 7/06* (2006.01)
*C12M 1/06* (2006.01)
(Continued)

(52) U.S. Cl.
CPC .......... *C12P 7/065* (2013.01); *B01F 3/04262* (2013.01); *B01F 7/00641* (2013.01); *B01F 7/1675* (2013.01); *B01F 7/18* (2013.01); *C12M 21/04* (2013.01); *C12M 21/12* (2013.01); *C12M 27/02* (2013.01); *C12M 29/04* (2013.01); *C12M 29/06* (2013.01); *C12M 29/08* (2013.01);
(Continued)

(58) Field of Classification Search
CPC . C12N 1/20; C12P 7/06; C12M 21/04; C12M 29/06; C12M 29/08; C12M 29/18; B01F 7/1675; B01F 7/18; B01F 3/04262; B01F 7/00641; B01F 2003/04326; Y02E 50/343; Y02E 50/17
USPC ............ 435/161, 291.6, 290.2, 813; 422/231
See application file for complete search history.

(56) References Cited

U.S. PATENT DOCUMENTS 5,173,429 A   12/1992  Gaddy
5,593,886 A    1/1997  Gaddy
(Continued)

FOREIGN PATENT DOCUMENTS

WO    WO 98/00558       1/1998
WO    WO 00/68407      11/2000
(Continued)

OTHER PUBLICATIONS

Riggs SS et al. (2006). Measuring Carbon Monoxide Gas-Liquid Mass Transfer in a Stirred Tank Reactor for Syngas Fermentation. Biotechnol. Prog., v22, pp. 903-906.*
(Continued)

*Primary Examiner* — Sean C. Barron
(74) *Attorney, Agent, or Firm* — James P. Krueger

(57) ABSTRACT

A process and apparatus is provided which are effective for improving CO mass transfer. The process includes introducing syngas into a reactor vessel through a gas sparger located below a liquid level in the reactor vessel. The syngas being introduced at a flow rate effective for maintaining a pressure inside of the reactor vessel of at least about 1 psig. An agitation energy of about 0.01 to about 12 kWatts/m³ medium is provided. The process is effective for providing a volumetric CO mass transfer coefficient of about 100 to about 1500 per hour.

11 Claims, 5 Drawing Sheets

Related U.S. Application Data filed on Jun. 30, 2011, provisional application No. 61/573,845, filed on Sep. 13, 2011.

(51) Int. Cl.
| | | |
|---|---|---|
| *C12M 1/00* | (2006.01) | |
| *B01F 7/18* | (2006.01) | |
| *B01F 3/04* | (2006.01) | |
| *B01F 7/16* | (2006.01) | |
| *B01F 7/00* | (2006.01) | |
| *C12M 1/107* | (2006.01) | |
| *C12N 1/20* | (2006.01) | |

(52) U.S. Cl.
CPC .............. *C12M 29/18* (2013.01); *C12N 1/20* (2013.01); *C12P 7/06* (2013.01); *B01F 2003/04326* (2013.01); *Y02E 50/17* (2013.01); *Y02E 50/343* (2013.01)

(56) References Cited

U.S. PATENT DOCUMENTS

| | | | |
|---|---|---|---|
| 5,807,722 | A | 9/1998 | Gaddy |
| 5,821,111 | A * | 10/1998 | Gaddy et al. .............. 435/252.5 |
| 5,888,806 | A * | 3/1999 | Nguyen .................... 435/291.3 |
| 5,972,661 | A | 10/1999 | Kubera |
| 6,136,577 | A | 10/2000 | Gaddy |
| 6,368,819 | B1 | 4/2002 | Gaddy |
| 6,500,651 | B1 | 12/2002 | Seress |
| 6,753,170 | B2 | 6/2004 | Gaddy |
| 7,201,884 | B2 | 4/2007 | Cohen |
| 7,285,402 | B2 | 10/2007 | Gaddy |
| 2001/0055237 | A1 | 12/2001 | Kubera |
| 2007/0275447 | A1 | 11/2007 | Lewis |
| 2010/0227377 | A1 | 9/2010 | Adams |
| 2010/0317077 | A1 | 12/2010 | Gaddy |
| 2013/0005010 | A1 | 1/2013 | Bell |
| 2013/0005021 | A1 | 1/2013 | Bell |

FOREIGN PATENT DOCUMENTS

| | | |
|---|---|---|
| WO | WO 2001/055237 | 12/2001 |
| WO | WO 02/08438 | 1/2002 |
| WO | WO 2007/117157 | 10/2007 |
| WO | WO 2009/022925 | 2/2009 |
| WO | WO 2009/023364 | 2/2009 |
| WO | WO 2009/064200 | 5/2009 |
| WO | WO 2009/112334 | 9/2009 |
| WO | WO 2009/113878 | 9/2009 |
| WO | WO 2009/154788 | 12/2009 |
| WO | WO 2010/227377 | 9/2010 |

OTHER PUBLICATIONS

Nielsen J and Villadsen J (2008). Bioreactors: Description and Modelling, in Biotechnology Set, Second Edition (eds H.-J. Rehm and G. Reed), Wiley-VCH Verlag GmbH, Weinheim, Germany.*
Han L et al. (2007). Gas-liquid mass transfer in a high pressure bubble column reactor with different sparger designs. Chemical Engineering Science, v62, pp. 131-139.*
Malestone ML and Arena U (2008). Olivine as a Tar Removal Catalyst During Fluidized Bed Gasification of Plastic Waste. AIChE Journal, v54(6), p. 1656-1667.*
Sardeing R et al. (2004). Gas-Liquid Mass Transfer; Influence of Sparger Location. Chemical Engineering Research and Design, v82(A9), p. 1161-1168.*
Bredwell, et al. "Mass-Transfer Properties of Microbubbles", Biotechnol 1. Experimental Studies, vol. 14, No. 1,6 Biotechnology Progress, Feb. 1998 pp. 31-38.
Cobb et al. "Production of Synthesis Gas by Biomass Gasification", Proceedings of the 2007 Spring National AIChE Meeting, Houston, Tx, Apr. 22, 2007.
Houben et al., "Tar Reduction Through Partial Combustion of Fuel Gas", Science Direct, Fuel 84(2005): 817-824.
Vander Der Hoeven et al., "Analysis of Hydrogen Influence on Tar Removal by Partial Oxidation", Science Direct, Fuel 85(2006);1.
Skidmore, "Syngas Fermentation Quantificatin of Assay Techniques, Reaction Kinetics, and Pressure Dependencies of the Clostridial P11 Hydrogenase," Thesis, Brigham Young Univ.
Kundiyana et al., "Syngas Fermentation in a 100-L Pilot Scale Fermentor: Design and Process Considerations," Journal Bioscience Bioengineering, vol. 109, #5, 492-8, 2010.
Datar, "Fermentation of Biomass Generated Producer Gas to Ethanol," Wiley InerScience, Apr. 15, 2004.
Ungerman et al., "Carbon Monoxode Mass Transfer for Syngas Fermentation in Stirred Tank Reactor with Dual Impeller Configurations, " Biotechnol, Prog. 2007, 23, 613-20.
Ismail et al., "Biological Hydrogen Production from CO: Bioreactor Performance," Biochemical Engineering Journal 39 (2008) 468-477.
Sioni, "Microbial Cell Factories, High Cell Density Media for *Escherichia coli* are generally Designed for Aerobic Cultivations-Consequences . . . ", BioMed Central, Aug. 7, 2008.
Mohammdi et al., "Bioconversion of Synthesis Gas to Second Generation Biofuels: A reivew;" Renewable and Sustainable Energy Reviews 15 (2011) 4255-4273.
International Searching Authority PCT/US2012/040322 Search Report and Written Opinion; Dec. 10, 2012.
International Searching Authority PCT/US2012/040327 Search Report and Written Opinion; Sep. 7, 2012.
International Searching Authority PCT/US2012/040319 Search Report and Written Opinion.

* cited by examiner

METHOD AND APPARATUS FOR SYNGAS FERMENTATION WITH HIGH CO MASS TRANSFER COEFFICIENT

This application claims the benefit of U.S. Provisional Application Nos. 61/571,564 and 61/571,565, both filed Jun. 30, 2011 and 61/573,845, filed Sep. 13, 2011, all of which are incorporated in their entirety herein by reference.

A process and apparatus is provided which are effective for improving carbon monoxide (CO) mass transfer. More specifically, factors including syngas quality, syngas sparging, reactor pressure and mixing are balanced to provide an improved volumetric CO mass transfer coefficient during syngas fermentation.

BACKGROUND

Anaerobic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

The CO is often provided to the fermentation as part of a gaseous substrate in the form of a syngas. Gasification of carbonaceous materials to produce producer gas or synthesis gas or syngas that includes carbon monoxide and hydrogen is well known in the art. Typically, such a gasification process involves a partial oxidation or starved-air oxidation of carbonaceous material in which a sub-stoichiometric amount of oxygen is supplied to the gasification process to promote production of carbon monoxide as described in WO 2009/154788.

Fermentation of gaseous substrates can be challenging because at least a portion of the gaseous substrate must dissolve in an aqueous fermentation broth before the substrate can be metabolized by the microbial culture. Fermentations where the gaseous substrate provides the carbon and energy source for the microorganism are particularly challenging due to the large amount of substrate needed to be solubilized in the fermentation broth before metabolism can take place. Substrates such as CO which have a low solubility in an aqueous fermentation broth require a highly efficient mass transfer into an aqueous fermentation broth as the CO provides a carbon source for the anaerobic fermentation. Attempts to improve CO mass transfer are described in U.S. Pat. Nos. 5,972,661 and 7,201,884 and in WO 2011/028137.

SUMMARY

Methods and apparatus are provided which are effective for improving a volumetric CO mass transfer coefficient during syngas fermentation. In one aspect, a process for fermentation of syngas is provided that includes introducing the syngas into a reactor vessel through a gas sparger or a gas distributor. The gas sparger is located below a liquid level in the reactor vessel and the syngas is introduced at a flow rate effective for maintaining a pressure inside of the reactor vessel of at least about 1 psig, and in another aspect, at least about 10 psig. The syngas has a $CO/CO_2$ molar ratio of at least about 0.75. An agitation energy is provided to the reactor vessel in an amount of about 0.01 to about 12 kWatts/m$^3$ medium. The process is effective for providing a STY of at least about 10 g ethanol/(L·day) and a volumetric CO mass transfer coefficient of about 100 to about 1500 per hour.

In another aspect, a process for fermentation of syngas is provided that includes introducing the syngas into a reactor vessel through a gas sparger. The gas sparger is located below a liquid level in the reactor vessel and the syngas is introduced at a flow rate effective for maintaining a pressure inside of the reactor vessel of at least about 1 psig, and in another aspect, at least about 10 psig. The syngas has a $CO/CO_2$ molar ratio of at least about 0.75, and in another aspect, the syngas has a CO content of at least about 20 mole %. The syngas is contacted with at least one gas dispersion impeller located above the gas sparger and the sygas is mixed with acetogenic bacteria with at least one mixing impeller located above the gas dispersion impeller. The gas dispersion impeller and mixing impeller are operably connected to an agitator through a drive shaft. The agitator provides an agitation energy input of about 0.3 to about 12 kWatts/m$^3$, in another aspect, about 0.7 to about 12 kWatts/m$^3$, and in another aspect, about 0.9 to about 12 kWatts/m$^3$ medium. The process is effective for providing a volumetric CO mass transfer coefficient of about 100 to about 1500 per hour.

In one aspect, the gas sparger includes holes having a diameter of 10 mm or less, and in another aspect, the holes have a diameter of 2.5 mm or less. Syngas may also be introduced at a flow rate effective for providing a gas velocity of 25 m/sec or greater at an exit of the holes and/or a pressure drop across the sparger holes of about 0.5 to about 2.5 psi.

In another aspect, a process is provided for improving a volumetric CO mass transfer coefficient. The process includes introducing the syngas into a reactor vessel through a gas sparger. The gas sparger is located below a liquid level in the reactor vessel and the syngas is introduced at a flow rate effective for maintaining a pressure inside of the reactor vessel of at least about 1 psig, and in another aspect, at least about 10 psig. The syngas has a $CO/CO_2$ molar ratio of at least about 0.75, and in another aspect, the syngas has a CO content of at least about 20 mole %. The syngas is contacted with at least one gas dispersion impeller and one mixing impeller. The gas dispersion impeller and mixing impeller are typically operably connected to an agitator through a drive shaft. The agitator provides an agitation energy input of about 0.3 to about 12 kWatts/m$^3$, in another aspect, about 0.7 to about 12 kWatts/m$^3$, and in another aspect, about 0.9 to about 12 kWatts/m$^3$ medium. The process is effective for providing a volumetric CO mass transfer coefficient of about 100 to about 1500 per hour.

A bioreactor is provided that includes a housing defining a reactor vessel, the reactor vessel effective for maintaining a pressure of at least about 1 psig, and in another aspect, at least about 10 psig. An agitator is disposed at least partially in the reactor vessel and at least partially below a liquid level in the reactor vessel. The agitator is operably connected to a drive shaft, the agitator effective for providing an agitation energy input of about 0.3 to about 12 kWatts/m$^3$, in another aspect, about 0.7 to about 12 kWatts/m$^3$; and in another aspect, about 0.9 to about 12 kWatts/m$^3$ medium. At least one mixing impeller operably is connected to the drive shaft and disposed below the liquid level of the medium and at least one gas dispersion impeller is operably connected to the drive shaft and disposed below the mixing impeller. A gas sparger is disposed below the gas dispersion impeller, the gas sparger including holes having a diameter of about 10 mm or less which are effective for providing a gas velocity of about 25 m/sec or greater at the exit of the holes. The bioreactor may further include a boot disposed at a lower end of the reactor vessel.

In another aspect, a bioreactor is provided that includes a housing defining a reactor vessel, the reactor vessel effective for maintaining a pressure of at least about 1 psig, and in another aspect, at least about 10 psig. An agitator is disposed at least partially in the reactor vessel and at least partially below a liquid level in the reactor vessel. The agitator is operably connected to a drive shaft, the agitator effective for providing an agitation energy input of about 0.3 to about 12 kWatts/$m^3$, in another aspect, about 0.7 to about 12 kWatts/$m^3$, and in another aspect, about 0.9 to about 12 kWatts/$m^3$ medium. At least one mixing impeller operably is connected to the drive shaft and disposed below the liquid level of the medium and at least one gas dispersion impeller is operably connected to the drive shaft and disposed below the mixing impeller. A gas sparger is disposed below the gas dispersion impeller, the gas sparger including holes having a diameter of about 10 mm or less which are effective for providing a gas velocity of about 25 m/sec or greater at the exit of the holes. The bioreactor further includes a boot disposed at a lower end of the reactor vessel, the boot including a boot sparger and boot mixer.

In another aspect, a process for fermentation of syngas is provided that includes inoculating acetogenic bacteria into a medium contained in a boot portion of a reactor vessel, the medium fills at least about 75% of a total volume of the boot. The acetogenic bacteria are contacted with syngas for a time effective for providing a cell density of at least about 5 grams per liter. Medium is added to the reactor vessel to provide a liquid level in the reactor vessel. Syngas is introduced into the reactor vessel through a gas sparger. The gas sparger is located below a liquid level in the reactor vessel. Syngas is introduced at a flow rate effective for maintaining a pressure inside of the reactor vessel of at least about 1 psig, and in another aspect about 10 psig. The syngas has a $CO/CO_2$ molar ratio of at least about 0.75 and is contacted with at least one gas dispersion impeller located above the gas sparger. Syngas and acetogenic bacteria are mixed with at least one mixing impeller located above the gas dispersion impeller. The gas dispersion impeller and mixing impeller are typically operably connected to an agitator through a drive shaft. The agitation energy input is about 0.3 to about 12 kWatts/$m^3$ medium. The process is effective for providing volumetric CO mass transfer coefficient of about 100 to about 1500 per hour.

In another aspect, a process for fermentation of syngas is provided that includes inoculating acetogenic bacteria into a medium contained in a boot portion of a reactor vessel, the medium effective for filling at least about 75% of a total volume of the boot. The acetogenic bacteria are contacted with syngas for a time effective for providing a cell density of at least about 3 grams per liter. Medium is added to the reactor vessel and cell density is maintained at about 3 grams per liter. Medium is added until a liquid level in the reactor vessel is obtained. Syngas is introduced into the reactor vessel through a gas sparger. The gas sparger is located below a liquid level in the reactor vessel. Syngas is introduced at a flow rate effective for maintaining a pressure inside of the reactor vessel of at least about 1 psig, and in another aspect about 10 psig. The syngas has a $CO/CO_2$ molar ratio of at least about 0.75 and is contacted with at least one gas dispersion impeller located above the gas sparger. Syngas and acetogenic bacteria are mixed with at least one mixing impeller located above the gas dispersion impeller. The gas dispersion impeller and mixing impeller are operably connected to an agitator through a drive shaft, the agitator providing an energy input of about 0.3 to about 12 kWatts/$m^3$ medium. The process is effective for providing volumetric CO mass transfer coefficient of about 100 to about 1500 per hour.

BRIEF DESCRIPTION OF FIGURES

The above and other aspects, features and advantages of several aspects of the process will be more apparent from the following drawings.

Figure 1:
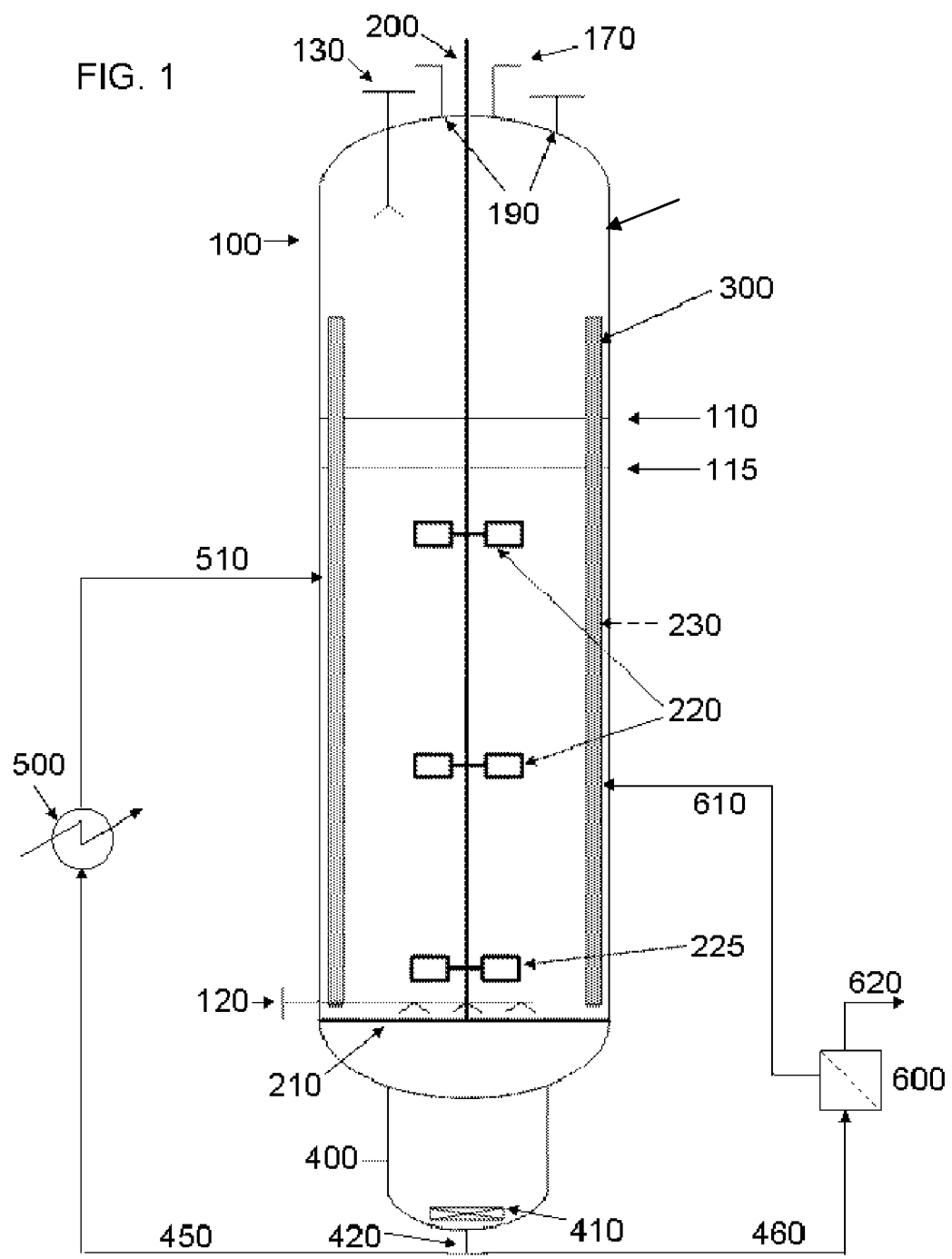
FIG. 1 is a perspective view of a bioreactor.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects of the present process and apparatus. Also, common but well-understood elements that are useful or necessary in commercially feasible aspects are often not depicted in order to facilitate a less obstructed view of these various aspects.

DETAILED DESCRIPTION

The following description is not to be taken in a limiting sense, but is made merely for the purpose of describing the general principles of exemplary embodiments. The scope of the invention should be determined with reference to the claims.

Syngas fermentation efficiency is improved by enhancing conditions for increasing the volumetric CO mass transfer coefficient. Methods and apparatus are provided that are effective for providing a volumetric CO mass transfer coefficient of about 100 to about 1500 per hour, in another aspect, about 200 to about 1100 per hour, in another aspect, about 200 to about 900 per hour, in another aspect, about 300 to about 800 per hour, in another aspect, about 400 to about 700 per hour, and in another aspect about 500 to about 600 per hour. Variables which affect the CO mass transfer coefficient include syngas sparging, reactor vessel pressure, syngas quality, and gas dispersion and mixing.

The processes described herein are effective for providing a high level of productivity. In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), and in another aspect, about 40 g ethanol/(L·day) to about 100 g ethanol/(L·day).

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

"Carbonaceous material" as used herein refers to carbon rich material such as coal, and petrochemicals. However, in this specification, carbonaceous material includes any carbon material whether in solid, liquid, gas, or plasma state. Among the numerous items that can be considered carbonaceous material, the present disclosure contemplates: carbonaceous material, carbonaceous liquid product, carbonaceous industrial liquid recycle, carbonaceous municipal solid waste (MSW or msw), carbonaceous urban waste, carbonaceous agricultural material, carbonaceous forestry material, carbonaceous wood waste, carbonaceous construction material, carbonaceous vegetative material, carbonaceous industrial waste, carbonaceous fermentation waste, carbonaceous petrochemical co products, carbonaceous alcohol production co-products, carbonaceous coal, tires, plastics, waste plastic, coke oven tar, fibersoft, lignin, black liquor, polymers, waste polymers, polyethylene terephthalate (PETA), polystyrene (PS), sewage sludge, animal waste, crop residues, energy crops, forest processing residues, wood processing residues, livestock wastes, poultry wastes, food processing residues, fermentative process wastes, ethanol co-products, spent grain, spent microorganisms, or their combinations.

The term "fibersoft" or "Fibersoft" or "fibrosoft" or "fibrousoft" means a type of carbonaceous material that is produced as a result of softening and concentration of various substances; in an example carbonaceous material is produced via steam autoclaving of various substances. In another example, the fibersoft can include steam autoclaving of municipal, industrial, commercial, and medical waste resulting in a fibrous mushy material.

The term "municipal solid waste" or "MSW" or "msw" means waste that may include household, commercial, industrial and/or residual waste.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas comprises use as an intermediate in producing synthetic petroleum for use as a fuel or lubricant via Fischer-Tropsch synthesis and previously the Mobil methanol to gasoline process. Syngas consists primarily of hydrogen, carbon monoxide, and some carbon dioxide, and has less than half the energy density (i.e., BTU content) of natural gas. Syngas is combustible and is often used as a fuel source or as an intermediate for the production of other chemicals.

The terms "fermentation", fermentation process" or "fermentation reaction" and the like are intended to encompass both the growth phase and product biosynthesis phase of the process. In one aspect, fermentation refers to conversion of CO to alcohol.

The term "mass transfer" as used herein relates to the transfer of atoms or molecules, particularly substrate atoms or molecules from a gaseous phase into an aqueous solution. A mass transfer coefficient may be calculated in accordance with the equations described in Younesi et al. (Iranian Journal of Biotechnology, Vol. 4, No. 1, January 2006), which is incorporated herein by reference. The following equation represents CO bioconversion ($X_{CO}$) and the volumetric mass transfer coefficient:

$$\frac{X_{CO}}{1 - X_{CO}} = \frac{RTV_L(k_L a)}{\pi H v_g}$$

$k_L a$: volumetric mass transfer coefficient
$X_{CO}$: % CO bioconversion
R: constant
T: temperature
$V_L$: liquid volume
H: Henry's constant (CO=1.226 liter·atm·mmol$^{-1}$)
$v_g$: gas volume The term "increasing the efficiency", "increased efficiency" and the like, when used in relation to a fermentation process includes increasing one or more of the rate of growth of microorganisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of fermentation.

Bioreactor Design

FIG. 1 is a perspective view of a bioreactor apparatus. The bioreactor apparatus includes a housing 105 defining a reactor vessel 100. The reactor vessel 100 may be substantially cylindrical and a cross section of the reactor vessel may be shaped in the form of a circle, substantially circular, or other shapes that are effective for improving mixing and mass transfer. The housing 105 may be formed of any materials know to withstand operating pressures of at least about 1 psig and up to pressures of at least about 250 psig and which is compatible with medium. In various aspects, the following pressures may be utilized, about 5 to about 200 psig, about 5 to about 100 psig, about 5 to about 50 psig, about 5 to about 25 psig, about 10 to about 200 psig, about 10 to about 100 psig, about 10 to about 50 psig, about 10 to about 25 psig, about 15 to about 200 psig, about 15 to about 100 psig, about 15 to about 50 psig, about 15 to about 25 psig, about 20 to about 200 psig, about 20 to about 100 psig, about 20 to about 50 psig, and about 20 to about 25 psig, Some examples of suitable materials include stainless steel, steel with a suitable inner liner and glass.

As further shown in FIG. 1, syngas enters the reactor vessel 100 through a gas inlet/distributor/sparger 120. Dispersion of the syngas and further mixing is accomplished with at least one gas dispersion impeller 225 and at least one mixing impeller 220 which are coupled to a drive shaft 200. The drive shaft 200 is supported by an agitator support plate 210. Gas is exhausted from the reactor vessel 100 through exhaust valve 170. The reactor vessel 100 may also include baffles 300 to further enhance mixing. In this aspect, the baffles 300 may be extended about 25% above an ungassed liquid level 115 to allow for a higher operating liquid level if the system is found to have low foaming.

In another aspect, the reactor vessel 100 may include addition ports 230. The addition ports 230 may include for example, one or more acidic addition ports, one or more alkaline addition ports, and one or more nutrient addition ports. In this aspect, the addition ports may be equally spaced apart around a circumference of the reaction vessel. The ports may be on the same or different horizontal plane. In one aspect, the reactor vessel 100 includes at least 4 equally spaced medium addition ports adjacent to a mixing impeller 220. The ports may be spaced around a circumference of the reactor vessel 100 at angles of 45° apart.

A gassed liquid level 110 and an ungassed liquid level 115 are maintained in the reactor vessel 100. Maintaining an ungassed liquid level 115 in the reactor vessel 100 allows for more efficient mass transfer and helps in maintaining control of foaming. In this aspect, an ungassed liquid level 115 is maintained in the reactor vessel 100 which is effective for providing a head space of at least about 1% of a total volume of the reactor vessel 100. In another aspect, the ungassed liquid level 115 provides a head space of about 1 to about 75% of a total volume of the reactor vessel 100. In various aspects, the head space may include the following percentages of the total volume of the reactor: about 5 to about 50%, about 10 to about 50%, about 15 to about 50%, about 20 to about 50%, about 25 to about 50%, about 30 to about 50%, about 30 to about 40% and about 30 to about 35%. The reactor vessel 100 may also include at least one liquid inlet 130 which aids in controlling foaming and allows for adjustment in reactor liquid volume. The liquid inlet 130 may be in the form of a spray nozzle. The reactor vessel 100 may also include additional ports 190.

As further illustrated in FIG. 1, the reactor vessel 100 may also include a boot 400 and a vortex breaker 410 disposed within the boot and over a medium outlet 420. The boot 400 and vortex breaker 410 are effective for preventing gas from being drawn out through the medium outlet 420. Medium drawn out through medium outlet 420 may be sent to a medium to recycle loop 450 or to a medium filter loop 460. Medium from the medium recycle loop 450 may be sent to a cooler/heat exchanger 500 and cooled medium 510 may be cycled back to the reactor vessel 100.

The boot 400 is effective for allowing gas bubbles to rise from the boot 400 back into the reactor vessel 100. In this aspect, liquid in the boot 400 should be as undisturbed as possible, and gas bubbles must rise out of the boot 400 faster than liquid is drawn down the boot. In this aspect, less than about 2% gas is drawn through the medium outlet 420 to a pump.

Medium from the medium filter loop 460 may be sent to a recycle filter 600. Concentrated cells 610 are returned to the reactor vessel 100 and permeate 620 is sent for further processing. Further processing may include separation of desired product such as for example ethanol, acetic acid and butanol.

In another aspect, the bioreactor may be configured without impellers. For example, the bioreactor may be configured as a gas lift type reactor or a bubble column type reactor. In these reactor configurations, an agitation energy of about 0.01 to about 12 kWatts/m$^3$ medium is provided.

Syngas and Syngas Sparging

Syngas is introduced into the bioreactor 100 through a gas inlet/sparger 120. Syngas may be provided from any know source. In one aspect, syngas may be sourced from gasification of carbonaceous materials. Gasification involves partial combustion of biomass in a restricted supply of oxygen. The resultant gas mainly includes CO and H$_2$. In this aspect, syngas will contain at least about 20 mole % CO, in one aspect, about 20 to about 100 mole % CO, in another aspect, about 30 to about 90 mole % CO, in another aspect, about 40 to about 80 mole % CO, and in another aspect, about 50 to about 70 mole % CO. The syngas will have a CO/CO$_2$ molar ratio of at least about 0.75. Some examples of suitable gasification methods and apparatus are provided in U.S. Ser. Nos. 61/516,667, 61/516,704 and 61/516,646, all of which were filed on Apr. 6, 2011, and all of which are incorporated herein by reference.

The bioreactor may include a CO concentration gradient where the CO concentration near the sparger is higher than the CO concentration at a higher level of the bioreactor. In this aspect, the bioreactor includes a ratio of CO concentration at a bottom level (sparger level) of the bioreactor to CO concentration at a top level of the bioreactor of about 100:1 to about 10:1.

One factor that may affect the mass transfer rate of the CO into the aqueous medium is the partial pressure of the gaseous substrate that includes the CO. In this aspect, the mass transfer rate can be increased by increasing the proportion of CO in a gas stream by enrichment or removal of unwanted components. In this aspect, the gas stream will have less than about 10 ppm oxygenated or non-oxygenated aromatics.

Figure 2A:
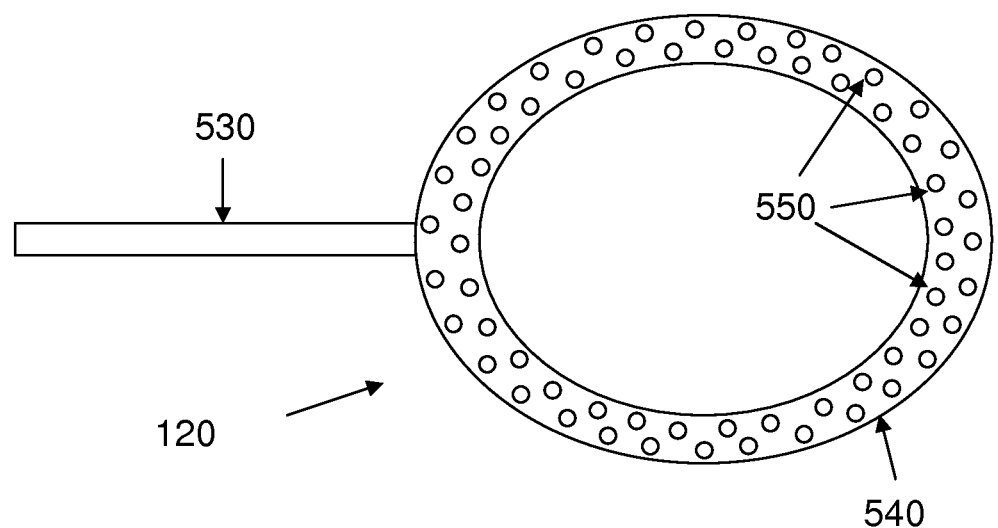
FIGS. 2A and 2B illustrate a bottom view of a gas inlet/sparger.
Figure 2B:
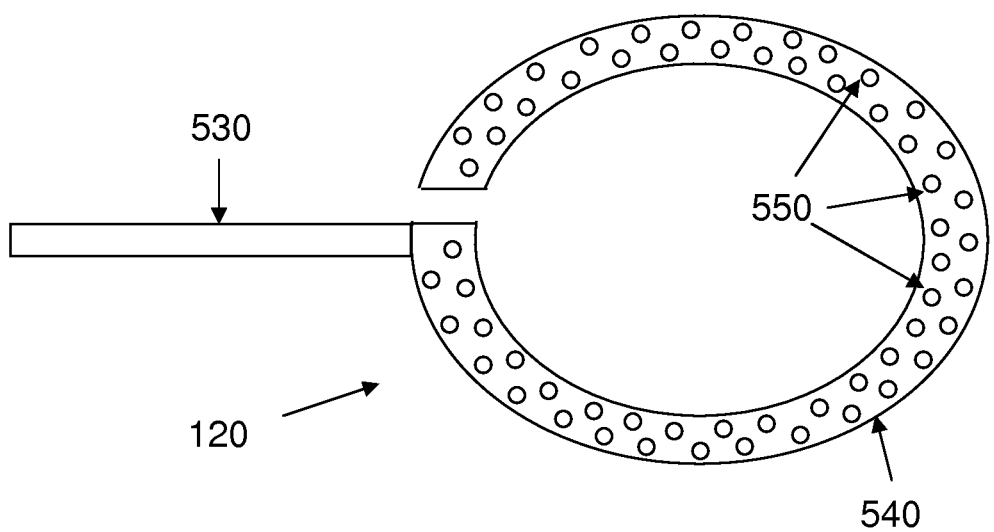

FIGS. 2A and 2B illustrate a bottom view of a gas inlet/sparger 120. In this aspect, the gas inlet/sparger 120 may include an inlet conduit 530 which is continuous with a sparger assembly 540. The sparger assembly 540 may be generally annular or circular as shown, or may be any other shape, such as for example, a straight, rectangular or free form. In the aspect where the sparger assembly 540 is annular in shape, the sparger assembly 540 has a diameter that is about 30 to about 100% of a diameter formed by the gas dispersion impellers 225, in various other aspects, about 40 to about 90%, about 40 to about 80%, and about 50 to about 70%.

The bottom portion of the gas sparger assembly 540 may include a plurality of holes 550. The holes 550 are of a diameter effective for providing a gas velocity of about 25 m/sec or greater at an exit of the holes, in another aspect, a gas velocity of about 25 m/sec to about 75 m/sec at an exit of the holes. In various aspects, the gas velocity may include the following ranges: about 25 to about 75 m/sec, about 25 to about 50 m/sec, about 25 to about 40 m/sec, about 25 to about 30 m/sec, about 30 to about 75 m/sec, about 30 to about 50 m/sec, about 30 to about 40 m/sec, about 35 to about 75 m/sec, about 35 to about 50 m/sec, about 35 to about 40 m/sec, about 40 to about 75 m/sec, about 40 to about 50 m/sec, and about 50 to about 75 m/sec. In this aspect, the holes will have a diameter of about 10 mm or less and in another aspect, a diameter of about 2.5 mm to about 1.0 mm.

Figure 3:
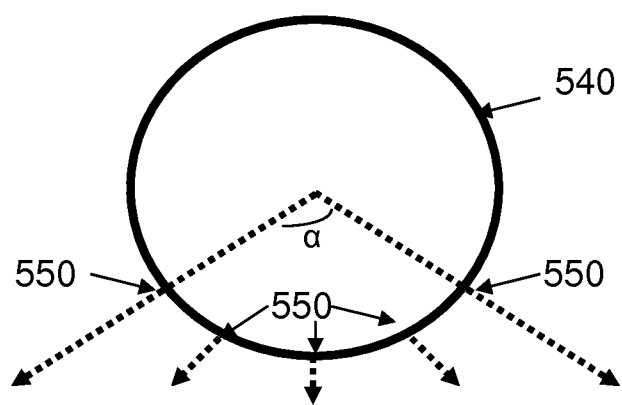
FIG. 3 is a cross sectional view of a gas sparger.

FIG. 3 illustrates a cross sectional view of a sparger assembly 540. In this aspect, dotted arrow lines show the flow of gas through hole 550. An angle of 120° is shown with lines drawn to a midpoint of the sparger assembly (shown as α). Holes may be located at any angle along the sparger assembly. In one aspect, the sparger assembly 540 includes about 1 to about 5 rows of parallel holes 550. Holes 550 are spaced apart and point in a downward direction. As shown in FIG. 3, the sparger assembly 540 includes 5 parallel rows of holes 550 and a total number of 790 holes spaced 30° apart. The downward pointing direction of the holes is effective for preventing fouling or clogging of the holes and helps to minimize back flow into the sparger assembly 540.

Gas Dispersion and Mixing

Referring again to FIG. 1, the reactor vessel 100 further includes a mixing assembly that includes a drive shaft 200, at least one mixing impeller 220, and at least one gas dispersion impeller 225. The mixing impeller 220 will generally be located below the liquid level 110. In one aspect, the reactor vessel 100 includes two or more mixing impellers 220. A gas dispersion impeller 225 is located below the mixing impeller 220. The reactor vessel 100 may include one or two or more gas dispersion impellers 225.

Figure 4A:
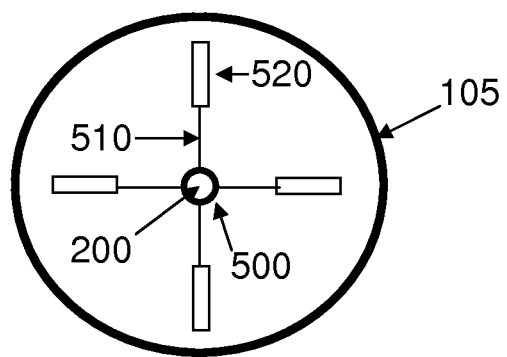
FIGS. 4A and 4B are top cross sectional views of a reactor vessel showing different impeller assemblies.
Figure 4B:
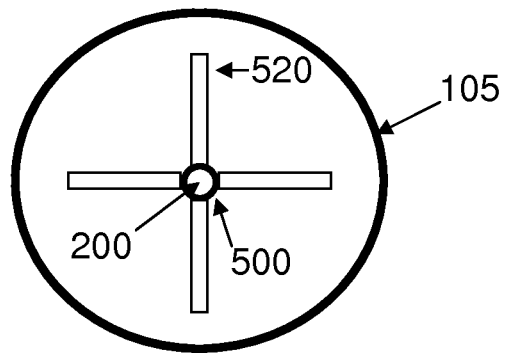

Referring now to FIG. 4A, each mixing and gas dispersion impeller assembly includes a hub 500 and a group of impellers arranged around the drive shaft 200. Each impeller includes an arm 510 attached to the hub 500 and holding one or more blades 520. The blades may be either mixing impeller or gas dispersion impellers. The mixing impeller assembly includes at least 2 blades and may include up to 6 blades. Examples of mixing impeller include low energy impellers such as marine impellers or marine propellers. In another aspect, the gas dispersion impeller assembly includes at least 2 blades and may include up to 6 blades. Examples of gas dispersion impellers include high energy impellers such as Rushton impellers or concave impellers. FIG. 4B is similar to FIG. 4A except that the blades 520 are attached directly to a hub 500.

Upon rotation of the drive shaft 200, syngas introduced through the gas inlet/sparger is entrained in small bubbles in the medium and travels around the generally circular cross section of the reactor vessel 100. The drive shaft is operably connected to and may be rotated with any suitable agitator, such as for example, an electric motor, a motor and gearbox, or a hydraulic motor. In this aspect, the agitator provides an energy input of about 0.3 to about 12 kWatts/m$^3$, in another aspect, about 0.7 kWatts/m$^3$ to about 12 kWatts/m$^3$, and in an important aspect, 0.9 kWatts/m$^3$ to about 12 kWatts/m$^3$ medium.

Bioreactor Operation

In accordance with one aspect, the fermentation process is started by addition of a suitable medium to the reactor vessel. The liquid contained in the reactor vessel may include any type of suitable nutrient medium or fermentation broth. The nutrient medium will include vitamins and minerals effective for permitting growth of the microorganism being used. Anaerobic medium suitable for the fermentation of ethanol using CO as a carbon source are known. One example of a suitable fermentation medium is described in U.S. Pat. No. 7,285,402, which is incorporated herein by reference.

The medium is sterilized to remove undesirable microorganisms and the reactor is inoculated with the desired microorganisms. In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui*, *Acetoanaerobium noterae*, *Acetobacterium woodii*, *Alkalibaculum bacchi* CP11 (ATCC BAA-1772), *Blautia producta*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei*, *Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum*, *Clostridium pasteurianum* (DSM 525 of DSMZ Germany), *Clostridium ragsdali* P11 (ATCC BAA-622), *Clostridium scatologenes*, *Clostridium thermoaceticum*, *Clostridium ultunense*, *Desulfotomaculum kuznetsovii*, *Eubacterium limosum*, *Geobacter sulfurreducens*, *Methanosarcina acetivorans*, *Methanosarcina barkeri*, *Morrella thermoacetica*, *Morrella thermoautotrophica*, *Oxobacter pfennigii*, *Peptostreptococcus productus*, *Ruminococcus productus*, *Thermoanaerobacter kivui*, and mixtures thereof.

Upon inoculation, an initial feed gas supply rate is established effective for supplying the initial population of microorganisms. Effluent gas is analyzed to determine the content of the effluent gas. Results of gas analysis are used to control feed gas rates. Upon reaching desired levels, liquid phase and cellular material is withdrawn from the reactor and replenished with medium. In this aspect, the bioreactor is operated to maintain a cell density of at least about 2 grams/liter, and in another aspect, about 2 to about 50 grams/liter, in various other aspects, about 5 to about 40 grams/liter, about 5 to about 30 grams/liter, about 5 to about 20 grams/liter, about 5 to about 15 grams/liter, about 10 to about 40 grams/liter, about 10 to about 30 grams/liter, about 10 to about 20 grams/liter, and about 10 to about 15 grams/liter. Cell density may be controlled through the recycle filter 600. In a related aspect, the bioreactor is operated to provide a liquid retention time of about 10 to about 400 hours, and in various aspect, about 10 to about 300 hours, about 10 to about 200 hours, about 10 to about 100 hours, about 10 to about 75 hours, about 10 to about 60 hours, about 10 to about 50 hours, about 10 to about 40 hours, about 10 to about 30 hours, and about 10 to about 20 hours. In this aspect, liquid retention time (LRT) may be calculated as follows:

$$LRT = \frac{\text{liquid volume}}{\text{net liquid volume flow rate (in or out)}}$$

Syngas is introduced into the bioreactor at a rate effective for maintaining a pressure in the bioreactor of at least about 1 psig, and in another aspect, a pressure of about 10 to about 250 psig. In various other aspect, the pressure may be about 10 to about 200 psig, about 10 to about 100 psig, about 10 to about 75 psig, about 10 to about 50 psig, about 10 to about 25 psig, about 20 to about 250 psig, about 20 to about 200 psig, about 20 to about 100 psig, about 20 to about 75 psig, about 20 to about 50 psig, about 20 to about 25 psig, about 30 to about 250 psig, about 30 to about 200 psig, about 30 to about 100 psig, about 30 to about 75 psig, about 30 to about 50 psig, about 40 to about 250 psig, about 40 to about 200 psig, about 40 to about 100 psig, about 40 to about 75 psig, about 40 to about 50 psig, about 50 to about 250 psig, about 50 to about 200 psig, about 50 to about 100 psig, and about 50 to about 75 psig.

In one aspect, in certain size fermentors, syngas is introduced into the gas inlet/sparger 120 at a rate of about 10 to about 50 ft$^3$/sec, and in another aspect, a rate of about 25 to about 35 ft$^3$/sec. Pressure is controlled through controlling the rate at which syngas is introduced in combination with controlling the rate at which gas is exhausted from the reaction vessel. Pressure may be measured in the reactor headspace or at the bottom of the reactor vessel.

In one aspect, sparger holes 550 and a pressure drop across the hole is important for improving the volumetric mass transfer rate of CO. A pressure drop across sparger holes 550 needs to be high enough to ensure distribution of gas bubble around the sparger assembly 540. In this aspect, sparging is effective to provide a pressure drop across the sparger holes 550 of about 0.5 psi to about 2.5 psi, and in another aspect about 1 psi to about 2 psi. The sparger holes 550 provide advantages over other forms of sparging. For example, sparger holes 550 are effective for avoiding fouling, as may occur with sintered metal spargers. Further, the sparger holes 550 are effective for providing consistent gas bubble sizes which contribute towards improved mass transfer.

Another factor that may affect the mass transfer rate is gas retention time. In this aspect, the bioreactor is effective for providing a gas retention time of at least about 2 minutes, and in another aspect, a gas retention time of about 2 minutes to about 15 minutes, in and in another aspect about 5 to about 10 minutes. Gas retention time (GRT) may be determined according to the following formula:

$$GRT = \frac{\text{liquid volume}}{\text{gas flow rate (in or out)}}$$

Temperature and ionic strength may also have an affect on the mass transfer rate. In this aspect, the temperature of the bioreactor is about 30 to about 50° C.

Figure 5:
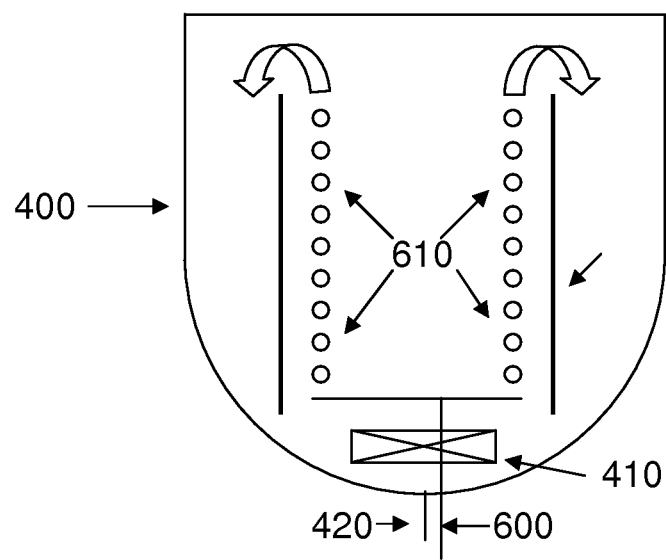
FIG. 5 illustrates an alternative configuration of the bioreactor boot.

An alternative configuration of the boot 400 is shown in FIG. 5. In this aspect, the boot 400 is utilized as a growth reactor during startup. The boot is configured to include a boot sparger 600. The boot also includes a boot mixer. The boot mixer may be configured with any known mixing apparatus. For example, gas mixing may be effected with impellers (not shown) or with a gas lift type fermentor equipped with a draft tube 620. As shown in FIG. 5, the gas lift fermentor is effective for circulating bubbles 610 and cells around the boot 400. Other reactor designs including a bubble type reactor, and external gas loop or jet type reactor may be utilized.

The alternative boot configuration is utilized by inoculating acetogenic bacteria into a medium contained in a boot portion of a reactor vessel. The medium in the boot fills at least about 75% of a total volume of the boot, in another aspect at least about 80%, in another aspect at least about 85%, in another aspect at least about 90%, and in another aspect at least about 95%. The boot is sparged with syngas and mixed for a time effective to provide a target cell density. In this aspect, the target cell density will be about 5 to about 40 grams/liter, and in various other aspects, about 5 to about 30 grams/liter, about 5 to about 20 grams/liter, about 5 to about 15 grams/liter, about 10 to about 40 grams/liter, about 10 to about 30 grams/liter, about 10 to about 20 grams/liter, and about 10 to about 15 grams/liter. Upon reaching a target cell density, medium levels are allowed to rise out the boot and into the reactor vessel to previously indicated levels. Sparging and mixing in the boot is stopped and the fermentation proceeds as previously described.

In another aspect, the cell density in the boot be brought to a level of at least about 3 grams per liter or any of the cell densities described herein. Upon reaching a cell density of at least about 3 grams per liter, medium is added at a rate effective to allow the cell density level to remain at a level of at least about 3 grams per liter. Upon reaching a desired medium level, sparging and mixing in the boot is stopped and the fermentation proceeds as previously described

EXAMPLE

Pilot plant scale fermentations were conducted to determine $k_L a$. The $k_L a$ was measured around 60 g ethanol/(L·day) STY (space time yield). An estimation of $k_L a$ was done by forcing the reaction under mass transfer limitation condition, or zero dissolved CO concentration. This was accomplished by effecting a temporary reduction in either gas flowrate or agitation rate so that there were an excess of cells for the gas available. Under these conditions, CO is reacted away as soon as it is dissolved so that the reaction is mass transfer limited. The CO dissolved into the solution is the same as the difference between the CO in the feedgas and the CO in the product. In a mass transfer limited system, this difference is the mass transfer rate at a given condition.

The basic equation utilized was $$k_L a = C_{kla}(P_g/V_l)^a v_{sg}^b$$

where $k_L a$=volumetric mass transfer coefficient (m$^3$ gas/s/m$^3$ liquid)

$C_{kla}$=Constant for a given system $P_g$=gassed agitator power consumption (W)

$V_l$=Liquid volume (m$^3$)

$v_{sg}$=superficial gas velocity (m/s)

a=scale up constant b=scale up constant

Runs were conducted at 6 psig (head pressure) and measurements were made at 60 g ethanol/(L·day) STY. Results were as follows:

| Run | kW | Cell Concentration (grams/liter) | CO Conversion % | $k_L a$ |
|---|---|---|---|---|
| 1 | 1.6 | 6.9 | 87.0 | 1151.2 |
| 2 | 1.7 | 6.9 | 86.3 | 938.7 |
| 3 | 1.6 | 6.7 | 86.7 | 842.3 |
| 4 | 1.6 | 6.3 | 88.2 | 721.1 |
| 5 | 1.3 | 6.1 | 76.7 | 1028.1 |
| 6 | 1.1 | 6.1 | 67.7 | 820.2 |
| 7 | 0.9 | 6.5 | 64.3 | 759.2 |
| 8 | 0.7 | 6.3 | 57.4 | 610.4 |
| 9 | 1.7 | 6.0 | 89.0 | 973.0 |
| 10 | 1.6 | 7.0 | 90.3 | 851.2 |

While the invention herein disclosed has been described by means of specific embodiments, examples and applications thereof, numerous modifications and variations could be made thereto by those skilled in the art without departing from the scope of the invention set forth in the claims.

What is claimed is:

1. A process for anaerobic fermentation of syngas, the process comprising:
   introducing the syngas into a stirred tank reactor vessel through a gas sparger, the gas sparger located below a liquid level in the reactor vessel, the syngas being introduced through holes in the gas sparger that point in a downward direction at a flow rate effective for providing a pressure drop across the sparger of about 0.5 to about 2.5 psi, a gas velocity of 25 m/sec or greater at an exit of the holes, and maintaining a pressure inside of the reactor vessel of at least about 1 psig, wherein the syngas has a $CO/CO_2$ molar ratio of at least about 0.75, and the process provides a gas retention time of about 5 to about 10 minutes, a liquid retention time of about 10 to about 400 hours, and a cell density of about 5 to about 40 grams per liter;
   contacting the syngas with at least one gas dispersion impeller located above the gas sparger; and
   mixing the syngas with at least one acetogenic bacteria with at least one mixing impeller located above the gas dispersion impeller,
   wherein the gas dispersion impeller and mixing impeller are operably connected to an agitator through a drive shaft, the agitator providing an agitation energy input of about 0.9 to about 12 kWatts/m³ medium,
   wherein the reactor vessel includes at least 4 equally spaced medium addition ports adjacent to the mixing impeller,
   wherein the process is effective for providing a volumetric CO mass transfer coefficient of about 200 to about 1100 per hour and an STY of about 20 to about 140 g ethanol/(L·day).

2. The process of claim 1 wherein the gas sparger includes holes pointing in a downward direction and having a diameter of 10 mm or less.

3. The process of claim 2, wherein the gas sparger includes holes having a diameter of 2.5 mm or less.

4. The process of claim 1 wherein syngas is introduced at a flow rate effective for maintaining a pressure inside of the reactor vessel of at least about 10 psig.

5. The process of claim 1 wherein the process is effective for providing a cell density of about 10 to about 40 grams per liter.

6. The process of claim 1 wherein the syngas has a CO content of at least about 20 mole %.

7. The process of claim 1 wherein the syngas includes less than about 10 ppm oxygenated or non-oxygenated aromatics.

8. The process of claim 1 wherein the acetogenic bacteria is selected from the group consisting of *Acetogenium kivui, Acetoanaerobium noterae, Acetobacterium woodii, Alkalibaculum bacchi* CP11 (ATCC BAA-1772), *Blautia producia, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

9. The process of claim 1 wherein the addition ports are spaced around a circumference of the reactor vessel at angles of about 45° apart.

10. The process of claim 1 wherein the reactor vessel includes baffles that extend about 25% above an ungassed liquid level.

11. The process of claim 1 wherein an ungassed liquid level is maintained in the reactor vessel to provide a head space of about 1% of a total volume of the reactor vessel.

* * * * *